United States Patent [19]

Sharpless et al.

[11] Patent Number: 5,332,843
[45] Date of Patent: * Jul. 26, 1994

[54] OPTICALLY ACTIVE DERIVATIVES OF GYCIDOL

[75] Inventors: Karl B. Sharpless, Brookline; Tetsuo H. Onami, Somerville, both of Mass.

[73] Assignee: Massachusetts Institute of Technology, Cambridge, Mass.

[*] Notice: The portion of the term of this patent subsequent to Oct. 6, 2009 has been disclaimed.

[21] Appl. No.: 917,499

[22] Filed: Jul. 21, 1992

Related U.S. Application Data

[63] Continuation of Ser. No. 563,793, Aug. 3, 1990, Pat. No. 5,153,338, which is a continuation of Ser. No. 878,176, Jun. 25, 1986, abandoned.

[51] Int. Cl.$^5$ .............................. C07D 303/34
[52] U.S. Cl. ..................... 549/551; 549/556
[58] Field of Search ................. 549/551, 556

[56] References Cited

U.S. PATENT DOCUMENTS

| | | | |
|---|---|---|---|
| 2,755,290 | 7/1956 | Mueller | 549/523 |
| 3,290,336 | 12/1966 | McClure | 549/520 |
| 4,210,653 | 7/1980 | Baldwin et al. | 549/520 |
| 4,346,042 | 8/1982 | Baldwin et al. | 549/520 |
| 4,471,130 | 9/1984 | Katsuki et al. | 549/523 |
| 5,153,338 | 10/1992 | Sharpless et al. | 549/551 |

FOREIGN PATENT DOCUMENTS

| | | |
|---|---|---|
| 71251 | 2/1983 | European Pat. Off. . |
| 157623 | 2/1983 | European Pat. Off. . |

OTHER PUBLICATIONS

K. Szabo et al., Chem. Abstracts, vol. 51 (1957) 1493c.
Chiral Building Blocks Article, Journal of Organic Chemistry, 50:25 (Dec. 13, 1985).
McClure et al., Journal of the American Chemical Society, 101:13 pp. 3666–3668 (Jun. 20, 1979).
Metzger, Mosaic, 16:1, Jan./Feb. 1985, pp. 34–41.
Sharpless, K. B., Chem. in Britain, 22:1 (Jan. 1986) pp. 38–40, 43–44.

*Primary Examiner*—Richard L. Raymond
*Attorney, Agent, or Firm*—George W. Neuner; Ronald I. Eisenstein

[57] ABSTRACT

Optically active derivatives of glycidol are disclosed. These novel compounds, (2S) and (2R) glycidyl m-nitrobenzenesulfonate and (2S) and (2R) glycidyl p-chlorobenzenesulfonate can be readily crystallized to high enantiomeric purity. Their use in other synthesis reactions is also described.

8 Claims, No Drawings

OPTICALLY ACTIVE DERIVATIVES OF GYCIDOL

This is a continuation of copending application(s) Ser. No. 07/563,793 filed on Aug. 3, 1990, now U.S. Pat. No. 5,153,338, which is a continuation of Ser. No. 06/878,176, filed on Jun. 25, 1986, now abandoned.

Optically active compounds have increasingly gained importance as ability to manipulate the synthesis of other optically active compounds has improved. A compound is optically active if its molecules are superimposable upon their mirror image. Isomers that are mirror images of each other are called enantiomers. Enantiomers have the same physical properties except for this difference in geometrical shape, i.e. mirror image. This difference however, has important consequences.

In living systems only one form of the stereoisomer generally functions properly. The other form either has no biological function or results in harm. In nature, the desired enantiomer is naturally synthesized. Synthesis chemists, in contrast, have rarely been as successful in making a pure enantiomer. They generally obtain racemic mixtures containing equal amounts of both optical forms of the molecule, i.e. dextrarotary (right-handed) and levorotary (left-handed).

Obtaining asymmetric molecules has traditionally involved physically or chemically resolving the desired molecule from a racemic mixture of the two different optical forms. A second method, the chiral pool method, involves using naturally occurring asymmetric molecules as building blocks for the desired asymmetric molecule. A third method has been developed which involves controlling the steps of the reaction so that only desired enantiomer is produced (See U.S. Pat. No. 4,471,130).

While the latter method has resulted in a tremendous advance in the field, problems still remain. The control over the reaction process is often not complete, and both forms of the molecule can still be produced. Even a small amount of the undesired form of the enantiomer results in significant loss of optical purity in the resultant mixture because an equal amount of the desired form of the enantiomer is associated with the undesired form. Thus, a step which produces 90% of the desired enantiomer only results in 80% enantiomeric excess (% e.e.). Consequently, it is extremely desirable to approach enantiomeric purity, and to have compounds that have high regioselectivity in substitution reactions.

The titanium-catalyzed asymmetric epoxidation of allylic alcohols has been important in further refining the above-described controlled step process. Homochiral glycidol has been useful in the synthesis of β-adrenergic blocking agents (β-blockers).

The in situ derivation of glycidol where the unstable glycidol is derivatized after completion of the asymmetric epoxidation reaction rather than isolated directly from the reaction mixture has many benefits. The derivatives are easier to handle, and they are more advanced synthetic intermediates than the parent glycidol. Glycidyl tosylate and glycidyl 4-nitrobenzoate are examples of such derived glycidols. However, the recrystallization of the crude mixture containing these glycidol derivatives has been difficult. The optical purity of these two derivatives has never approached 100%. In fact, the purity of the glycidyl 4-nitrobenzonate derivative has not risen above 92% e.e., and glycidyl tosylate, even if carefully crystallized several times (although increasing in % e.e.), usually ends up near 95% e.e. With other glycidol derivatives it has proven extremely difficult to improve the enantiomeric purity by crystallization.

We have now discovered two compounds that can more easily reach enantiomeric purity.

The two compounds are (2S)-glycidyl m-nitrobenzenesulfonate and (2S)-glycidyl p-chlorobenzenesulfonate. These compounds can readily be produced from allylic alcohol, and crystallized to extremely high enantiomeric purity.

The compounds are produced by the following reaction schemes:

A. GLYCIDYL m-NITROBENZENESULFONATE

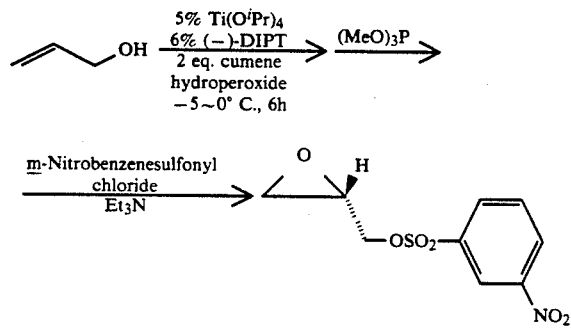

3. GLYCIDYL p-CHLOROBENZENESULFONATE

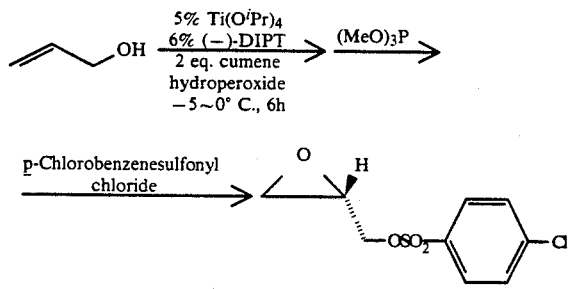

The (2S)-glycidyl m-nitrobenzenesulfonate preferably is purified to at least about 94% e.e., preferably at least about 96% e.e., and even more preferably at least about 98% e.e. Yields up to 98.8% e.e have been obtained in accord with this invention. The purity of the (2S)-glycidyl p-chlorobenzenesulfonate is preferably at least about 94% e.e. and more preferably at least about 95% e.e. Purification is obtained by using crystallization techniques which are well known in the art.

(2R)-glycidyl m-nitrobenzenesulfonate and (2R)-glycidyl p-chlorobenzenesulfonate can be similarly produced by using (+)-DIPT instead of (−)-DIPT. (2R) compounds can be purified to the same enantiomeric purity as (2S) compounds.

The crystallized compound is stable and can easily be scored at room temperature until its use is desired. The stability of these compounds means that they can be used commercially as "starting materials" in the synthesis of, for example, β-blockers. For example, a convenient, one-pot procedure can be employed to convert the glycidyl m-nitrobenzenesulfonate into an important intermediate to the β-blocker, propranolol, which can be converted to propranol by the addition of $^iPrNH_2$ and $H_2O$ in the reaction mixture

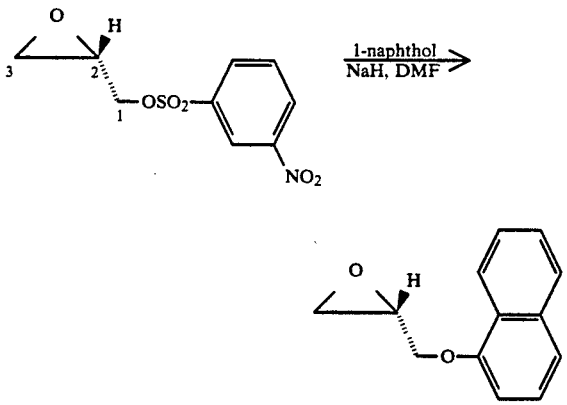

This substitution reaction takes place with extremely high regioselectivity, approaching 100:0 ($C_1:C_3$). The same reaction scheme can be used for converting the glycidyl p-chlorobenzenesulfonate.

Other intermediates to β-blockers, β-blockers or related compounds can be readily made according to the following reaction scheme:

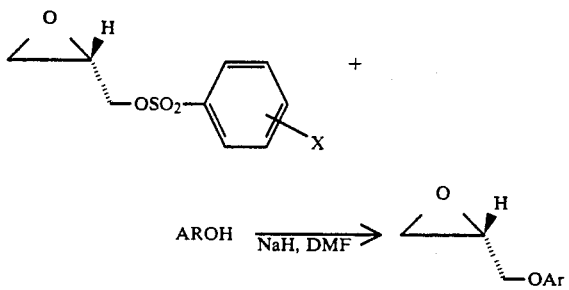

where X is m-nitro or p-chloro substituent and ArOH is an aromatic alcohol. Any aromatic alcohol capable of displacing the sulfonate moiety can be used in the reaction to create the desired intermediate. Preferable aromatic alcohols are those that yield desired β-blockers upon subsequent reaction with a predetermined amine. The appropriate amine to use can be readily determined by the person of ordinary skill in the art.

The invention will be further illustrated by the examples that follow:

General

Crushed 3 Å molecular sieves (Aldrich Chemical Co.) were activated by heating in a vacuum oven at 160° C. and 0.05 mm Hg for at least 8 hours. Diisopropyl tartrate and titanium (IV) isopropoxide (Aldrich) were distilled under vacuum and were stored under an inert atmosphere. Allyl alcohol and cumene hydroperoxide (tech., 80%, Aldrich) were dried prior use over 3 Å molecular sieves, but otherwise used as received. Dichloromethane (EM Reagent) was not distilled, but was also dried over 3 Å molecular sieves. 1-Naphthol (Aldrich) was sublimed prior to use.

Melting points were determined on a Thomas Hoover capillary melting point apparatus and are uncorrected. IR spectra were recorded on a Perkin-Elmer 597 spectrophotometer. $^1$H NMR spectra were recorded on a Bruker WM-250 (250 MHz) spectrometer with tetramethylsilane as an internal standard.

EXAMPLE 1

Preparation of (2S)-Glycidyl m-nitrobenzenesulfonate

An oven-dried 500-mL three-necked flask equipped with a magnetic stirrer, low-temperature thermometer, and rubber septums, was charged with activated 3 Å powdered sieves (3.5 g) and 190 ml dichloromethane under nitrogen. D-(−)-Diisopropyl tartrate (DIPT) (1.40 g, 6 mmol) was added via cannula as a solution in 1.5 ml $CH_2Cl_2$, washing with an additional 1 ml $CH_2Cl_2$. Allyl alcohol (6.8 ml, 5.81 g, 0.1 mol) was then added, the mixture cooled to −5° C. and Ti(OiPr)$_4$ (1.50 ml, 1.43 g, 5 mmol) added via syringe. After stirring for 30 minutes, precooled (ice bath) cumene hydroperoxide (80%, 3.5 ml, ca. 0.2 mol) was added via cannula over a period of one hour maintaining an internal temperature of ≦−2° C. The reaction mixture was stirred vigorously under nitrogen at −5° to 0° C. for six hours. After cooling −20° C. trimethyl phosphite was added very slowly via cannula, not allowing the temperature to rise above −10° C., and carefully monitoring the reduction of hydroperoxide [TLC in 40% EtOAc/hexane; tetramethyl phenylenediamine spray indicator (1.5 g in MeOH:H$_2$:HOAc 128:25:1 ml); ca. 14.1 ml (14.89 g, 0.12 moles) of P(OMe)$_3$ were required for complete reduction. Further excess should be avoided.] The reaction is quite exothermic and addition took one hour resulting in formation of stock solution A.

One fifth of the reaction mixture (stock solution A) (43 ml) was transferred into a 100-ml round-bottomed flask using a syringe, and triethylamine (4.2 ml, 2.05 g, 30 mmol) was added at −20° C., followed by addition of m-nitrobenzenesulfonyl chloride (4.43 g., 20 mmol) as a solution in 8 ml dichloromethane. The flask was stoppered and transferred to a freezer at −20° C.

After 10 hours the reaction mixture was allowed to warm gradually to room temperature, then filtered through a pad of Celite, washing with additional dichloromethane. The resultant yellow solution was washed with 10% tartaric acid, followed by sat. brine, dried (MgSO$_4$) and concentrated to afford an oil, from which volatile components (e.g. cumene, 2-phenyl-2-propanol, P(OMe)$_3$, OP(OMe)$_3$, etc.) were removed under high vacuum at 65° C. on a rotary evaporator equipped with a dry ice condenser. The residue was filtered through a short pad of silica gel (ca. 1 g per g crude oil), eluding with dichloromethane. Concentration gave a lemon yellow oil which was dissolved in ca. 18 mt warm Et$_2$O and crystallized by addition of hexane to give 2.932 g (56.6% yield) of (2S)-glycidyl m-nitrobenzenesulfonate, m.p. 54°-60° C. (96% e.e.).

Attempts to measure the e.e. directly, via $^1$H NMR in the presence of chiral shift reagents, or by HPLC on a chiral stationary phase, proved unsuccessful. Therefore, glycidyl m-nitrobenzenesulfonate was converted to the corresponding iodohydrin, following Conforth's published procedure (J. Chem. Soc. (1959), 112). The crude iodohydrin was then directly esterified with (E)-(+)-α-methoxy-α-(trifluoromethyl) phenylacetyl chloride to give the Mosher ester, and the e.e. measurement was made by HPLC of the ester on a chiral Pirkle column, eluting with 8% iso-proponal/hexane. The e.e. was also determined by $^1$H NMR analysis of the Mosher ester in $C_6D_6$.

A part of the crystals (2.635 g) was recrystallized twice from ethanol to afford 1.745 g of pure crystals, m.p. 63°-64° C.; [[α]$_D^{23}$+23.0 (C=2.14, CHCl$_3$); 99% e.e.

IR (KBr) 3114, 3090, 1611, 1532, 1469, 1451, 1428, 1354, 1280, 1257, 1188, 1132, 1086, 1076, 1004, 981, 963, 919, 913, 889, 867, 842, 820, 758, 739, 674, 667, 596, 585, 549, 524, 447, 430, 405 cm$^{-1}$.

NMR (250 MHz, CDCl$_3$) δ 8.79 (t, J=1.5 Hz, 1H), 8.54 (m, 1H), 8.28 (m, 1H), 7.82 (t, J=8.0, 8.0 Hz, 1H), 4.50 (dd, J=3.4, 11.4 Hz, 1H), 4.04 (dd, J=6.0, 11.4 Hz, 1H), 3.23 (m, 1H). 2.86 (t, J=4.5, 4.5 Hz, 1H), 2.64 (dd, J=2.5, 4.75 Hz, 1H).

EXAMPLE 2

Substitution Reaction

In a 5-ml round-bottomed flask equipped with a rubber septum, sodium hydride (oil free, 24 mg, 1 retool) was suspended in DMF (1 ml, stored over 3Å sieves) at room temperature under a nitrogen atmosphere. 1-Naphthol (121 mg, 0.84 mmol) was added as a solution in DMF (0.5 ml) to produce a foamy green sludge. After 15-30 minutes, a solution of (2S)-glycidyl m-nitrobenzenesulfonate (98.8% e.e., 207 mg, 1 mmol in 0.5 ml DMF) was added. A clear green-brown solution resulted.

After 30 minutes the reaction was judged to be complete by TLC (silica gel, 40% EtOAc/hexane).

The reaction mixture was diluted with water (5 ml) and extracted with ether (3×10 ml). The combined extracts were washed with sat. brine, dried over anhydrous sodium sulfate and concentrated in vacuo to give crude crystalline glycidyl 1-naphthyl ether (98.8% e.e.). The e.e. was determined by NMR analysis (DCl$_3$) of the Mosher ester, which was prepared from the crude glycidyl 1-naphthyl ether according the method described in Example 1.

EXAMPLE 3

Preparation of (2S)-glycidyl p-chlorobenzenesulfonate

One fifth of stock solution A (43 ml) from Example 1 was transferred into a 100 ml round-bottomed flask using a syringe and triethylamine (4.2 ml, 3.05 g, 30 mmol) was added at −20° C., followed by the addition of p-chlorobenzenesulfonyl chloride (4.22 g, 20 mmol). Thereafter, the (2S)-glycidyl p-chlorobenzenesulfonate was prepared according to the procedure of Example 1.

The crystals were obtained by crystallization of the extracts from ether-hexane (37.5% yield), m.p. 60.7°-62.3° C. (94% e.e.), which was recrystallized from ethanol-hexane to afford pure crystals, m.p. 61°-62.5° C.; [α]$_D^{23}$+22.6 (C=2.02, CHCl$_3$); 95.2% e.e.

IR (KBr) 3100, 1572, 1478, 1452, 1399, 1360 1281, 1260, 1180, 1136, 1089, 1019, 960, 917, 868, 826, 770, 754, 709, 628, 576, 531, 489, 448 cm$^{-1}$.

NMR (250 MHz, CDCl$_3$) δ 7.87 (d, J=8.0 Hz, 2H), 7.55 (d, J=8.0 Hz, 2H), 4.34 (dd, J=3.4, 11.6 Hz, 1H), 3.97 (dd, J=6.0, 11.4 Hz, 1H), 3.21 (m, 1H), 2.84 (T, J=4.5, 4.5 Hz, 1H), 2.62 (dd, J=2.5, 4.75 Hz, 1H).

This invention has heed described in detail including the preferred embodiments thereof. However, it will be appreciated that chose skilled in the art, upon consideration of this disclosure, may make modifications and improvements thereon without departing from the spirit and scope of the invention as set forth in the claims.

We claim:

1. A compound of the formula

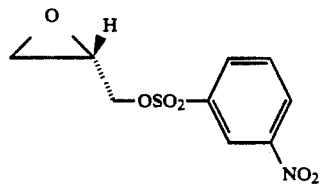

purified to at least about 96.0% e.e.

2. The compound of claim 1 purified to at least about 98.8% e.e.

3. A compound of the formula

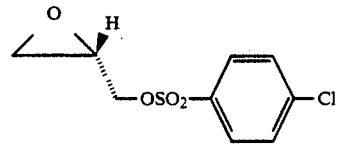

4. The compound of claim 3, purified to at least about 95.0% e.g.

5. A compound of the formula

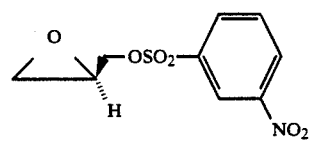

purified to at least about 96.0% e.e.

6. The compound of claim 5 purified to at least about 98.8% e.g.

7. A compound of the formula

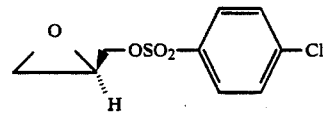

8. The compound of claim 7 purified to at least about 95.0% e.e.

* * * * *